United States Patent [19]

Wood

[11] 4,032,605

[45] June 28, 1977

[54] ALPHA-HALO SUBSTITUTED DIACYL PEROXIDES

[75] Inventor: Donald W. Wood, Concord, Calif.

[73] Assignee: Argus Chemical Corporation, Brooklyn, N.Y.

[22] Filed: Dec. 6, 1971

[21] Appl. No.: 205,387

Related U.S. Application Data

[63] Continuation-in-part of Ser. No. 675,360, Oct. 16, 1967, Pat. No. 3,652,681.

[52] U.S. Cl. .................... 260/610 D; 260/348 R; 260/92.8 R; 526/227; 526/344
[51] Int. Cl.² .................................. C07C 179/14
[58] Field of Search .......... 260/610 D, 468, 348 R, 260/478, 479, 333

[56] References Cited

UNITED STATES PATENTS

| | | | |
|---|---|---|---|
| 2,775,618 | 12/1956 | Dittman et al. | 260/610 D |
| 2,865,904 | 12/1958 | Seed et al. | 260/610 D |
| 3,397,245 | 8/1968 | Appell | 260/610 D |

FOREIGN PATENTS OR APPLICATIONS

| | | | |
|---|---|---|---|
| 699,768 | 12/1964 | Canada | 260/610 D |

Primary Examiner—James O. Thomas, Jr.
Assistant Examiner—W. B. Lone
Attorney, Agent, or Firm—Townsend and Townsend

[57] ABSTRACT

Asymmetrical organic diacyl peroxide polymerization initiators having enhanced initiator efficiency and characterized by the presence of an acyclic acyl group of four or more carbon atoms having bromo or halo substitution at the alpha carbon atom, the other acyl group being different and heterosubstituted. However, when the alpha-halosubstituted acyl group is branched chain the other acyl group may be hydrocarbon.

12 Claims, No Drawings

ALPHA-HALO SUBSTITUTED DIACYL PEROXIDES

CROSS REFERENCES TO RELATED APPLICATIONS

This application is a continuation-in-part application of application Ser. No. 675,360, filed Oct. 16, 1967, now U.S. Pat. No. 3,652,681 whose disclosure is incorporated herein by reference.

BACKGROUND OF THE INVENTION

1. Field of the Invention

Among the primary uses of peroxides is the initiation of polymerization of ethylenically unsaturated monomers, e.g. vinyl chloride. Peroxidic initiators have been available and used for a long time, so that continued efforts in this area have been directed toward providing small improvements in performance. Considerations in developing catalysts are the temperature of decomposition, the efficiency of initiation, storage temperature and shelf life, the degree of self-induced decomposition, and any detracting features which may be imparted to the polymer, such as inhomogeneous curing, etc.

In many instances, it is desirable to carry out polymerizations at relatively low temperatures. Therefore, catalysts must be found which provide a reasonable rate of initiation of the polymerization at the desired polymerization temperature.

2. Description of the Prior Art

U.S. Pat. Nos. 2,865,904 and 3,089,865 describe halogenated acyl peroxides.

SUMMARY OF THE INVENTION

Novel peroxidic compounds are provided which are asymmetrical diacyl peroxides having as one acyl group, an acyclic alpha-halosubstituted aliphatic group of at least four carbon atoms, either branched or straight chain, and a second acyl group, different than the first acyl group, which when the first acyl group is straight chain has at least one heteroatom other than the oxygen of the acyl functionality, the heteroatom usually being oxygen or halogen.

DESCRIPTION OF THE SPECIFIC EMBODIMENTS

The novel peroxidic compounds of this invention, which find use as catalysts in initiating the polymerization of addition polymerizable monomers, are asymmetrical diacyl peroxides, having one acyl group with alpha-halosubstitution, particularly bromine or chlorine. By asymmetrical it is intended that the two acyl groups on opposite sides of the peroxide functionality are different.

The molecule will normally have at least six carbon atoms and not more than 36 carbon atoms, usually having from six carbon atoms to about 20 carbon atoms. The total number of heteroatoms, usually oxygen or halogen, other than the oxygen atoms involved in the acyl and peroxide functionalities, will be at least one when the alpha-halosubstituted acyclic acyl functionality is branched and will be at least two when the alpha-halosubstituted acyclic functionality is straight chain, and usually not more than eight, more usually not more than six. If there is only one halo functionality as the sole hetero substituent, it will usually be chlorine or bromine. When there is more than one halo functionality, the halogen may be of atomic number in the range of nine to 35, i.e., fluorine, chlorine or bromine.

Heterosubstituents containing oxygen may be present as alcohols, ethers, (acyclic or cyclic), esters, or ketones usually ethers or esters.

With the straight chain, acyclic alpha-halosubstituted acyl group, there will normally be from one to three hetero substituents on the other acyl group, more usually from one to two, while with the branched chain alpha-halosubstituted acyclic acyl group there will normally be on the other acyl group, from zero to three heterosubstituents, more usually from zero to one.

The alpha-halosubstituted acyclic acyl group will usually be saturated aliphatic of from four to 21 carbon atoms, more usually of from four to 12 carbon atoms, having chain lengths including the carbonyl group of from four to 12, more usually of from four to 10 and when branched will usually have from one to five branches, more usually from one to three branches, normally of from one to two carbon atoms, and usually methyl. The other acyl group, which may be substituted or unsubstituted, depending on the nature of the alpha-halosubstituted acyclic acyl group, may be aliphatic, alicyclic, aromatic or combinations thereof, e.g. aralkyl and alkaryl, and will usually be of from two to 21 carbon atoms, more usually of from two to 12 carbon atoms. The group may be aliphatically saturated or unsaturated, preferably saturated, and will normally have not more than two sites of aliphatic unsaturation, e.g., ethylenic or acetylenic. Usually, there will be from zero to two rings, either fused or non-fused.

The above compounds are particularly effective catalysts for polymerization of addition polymerizable ethylenically unsaturated monomers. The compounds have superior capability at relatively moderate temperatures in providing substantial conversion of the monomer to polymer.

For the most part, the compounds of this invention will have the following formula:

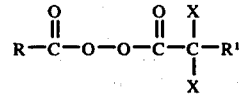

wherein X is hydrogen, chlorine or bromine, at least one X being chlorine or bromine; $R^1$ is saturated aliphatic hydrocarbon, either straight chain or branched chain of at least two carbon atoms, and not more than 19 carbon atoms, more usually of from two to 10 carbon atoms usually having from zero to five branches, more usually from zero to three branches, the branches normally being of from one to two carbon atoms and preferably one carbon atom, i.e., methyl; R is an organic radical composed solely of carbon, hydrogen, oxygen and halogen of atomic number nine to 35; (fluorine, chlorine and bromine), more usually 17–35; depending on the nature of $R^1$, straight or branched chain, R will have from zero to six heteroatoms or one to six heteroatoms, more usually from zero to three heteroatoms or one to three heteroatoms, preferably zero to two or one to two heteroatoms respectively.

R may be aliphatic, alicyclic, aromatic or combinations thereof, straight or branched chain, aliphatically saturated or unsaturated. Normally, there will be from zero to two sites of aliphatic unsaturation, more usually from zero to one site, i.e., ethylenic or acetylenic.

As already indicated, the R group will vary in scope, depending on the nature of $R^1$. When $R^1$ is branched chain, R may be substituted hydrocarbon or hydrocarbon. When $R^1$ is straight chained, R may be only substituted hydrocarbon, the substituents being either oxygen or halogen. Normally, any halogen will be at a site other than the alpha position when R is aliphatic. R may be of from one to nineteen carbon atoms, usually is of from one to 11 carbon atoms and preferably is of from one to seven carbon atoms.

When $R^1$ is straight chain, R will usually be of at least two carbon atoms.

When R is aromatic it will usually be of from six to 10 carbon atoms, and hydrocarbon or halohydrocarbon of from one to three halogen atoms, particularly chlorohydrocarbon of from one to two chlorine atoms.

The oxygen substituent may be present as hydroxyl, ethereal, either in a chain or in a ring, keto or ester, preferably as an ether, either in an acyclic chain or as epoxy, or as an ester. Usually, there will be from one to three heterocontaining substituents, more usually from one to two and preferably only one.

Illustrative $R^1$ groups include ethyl, propyl, isopropyl, isobutyl, isopentyl, tert.-butyl, neopentyl, isooctyl, isodecyl, 1,3-dimethylbutyl, etc.

Illustrative R groups, when R is hydrocarbon, include methyl, ethyl, propyl, isopropyl, cyclopentyl, cyclohexyl, cyclohexenyl, allyl, 1-propenyl, phenyl, naphthyl, tolyl, decyl, dodecyl, dodecenyl, etc. Illustrative R groups, when R contains heterosubstituents includes 2-chloroethyl, 2-chloropropyl, 2-bromopropyl, 3-bromopropyl, 3-chloroallyl, 4-chlorobutyl, ω-bromononyl, 4-chlorocyclohexyl, 4-bromophenyl, para-bromo-ortho-tolyl, 3-methoxypropyl, methoxymethyl, ethoxyethyl, 2,3-epoxypropyl, 3,4-epoxybutyl, 2-tetrahydrofuranyl, 2-ethoxycarbonylethyl, 3-phenoxycarbonylpropyl, para-anisyl, para-phenetyl, 2-chloro-4-methoxyphenyl, para-trifluoromethylphenyl, 2,2,2-trichloroethyl, 2,3-dibromopropyl, 3-(para-chlorophenoxycarbonyl)propyl, etc.

Illustrative compounds include 2-bromo-3-methylbutanoyl acetyl peroxide, 2-chloro-3,5,5-trimethylhexanoyl acetyl peroxide, 2-chloro-3,5,5-trimethylhexanoyl benzoyl peroxide, 2-chloro-3-methylbutanoyl acetyl peroxide, 2,2-dichloro-3,5,5-trimethylhexanoyl propanoyl peroxide, 2-chloro-3-methylbutanoyl crotonyl peroxide, 2-bromo-3-methylbutanoyl 2-methoxypropanoyl peroxide, 2-chloro-3-methylbutanoyl ethoxyacetyl peroxide, 2-chloro-8-methynonanoyl 3,3,3-trifluoropropanoyl peroxide, 2-chlorobutanoyl 3,4-epoxybutanoyl peroxide, 2-chloropentanoyl 3-ethoxycarbonylpropanoyl peroxide, 3-bromopentanoyl 3-phenoxycarbonylpropanoyl peroxide, 2-chlorobutanoyl 3-ethoxycarbonyl-2,3-dimethylpropenoyl peroxide, 2,2-dibromo-4-methylpentanoyl m-chlorobenzoyl peroxide, 2-chloro-5-methylhexanoyl p-trifluoromethylbenzoyl peroxide, 2-chlorobutanoyl benzoylacetyl peroxide, 2,2-dichlorobutanoyl anisoyl peroxide, 2-chloro-10-methylundecanoyl 2-chloro-4-tert.-butoxybenzoyl peroxide, 2-chlorobutanoyl p-trichloromethylphenylacetyl peroxide, etc.

One preferred embodiment within the subject invention has the following formula:

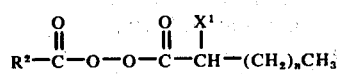

wherein $X^1$ is chlorine or bromine; $n$ is an integer of from one to nine, preferably of from one to three; and $R^2$ is an organic radical having other than alphahalosubstitution and of from two to eleven carbon atoms, more usually of from two to seven carbon atoms, having from one to three heteroatoms which are halogen of atomic number nine to 35, more usually from 17-35 or oxygen as an ether (including epoxy) or ester functionality. $R^2$ is aliphatic, alicyclic or aromatic, or combinations thereof, usually aliphatic or aromatic. Preferably, $R^2$ will have not more than one site of aliphatic unsaturation and usually will be free of aliphatic unsaturation.

A second preferred embodiment will have the following formula:

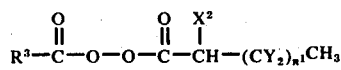

wherein $X^2$ is chlorine or bromine, Y is hydrogen or alkyl of one– three carbon atoms, at least one Y being alkyl and usually not more than five Y's being alkyl, more preferably, the alkyl groups are on other than adjacent carbon atoms; $n^1$ is an integer of from 1 to 6; and $R^3$ is an organic radical composed solely of carbon, hydrogen, halogen of atomic number nine to 35 and oxygen, preferably hydrocarbon or halohydrocarbon having from one to three, more usually from one to two halogen substituents in other than the alpha position and may be aliphatic, alicyclic or aromatic but is preferably aliphatic. $R^3$ will normally be of from one to eleven carbon atoms, more usually from one to seven carbon atoms, and preferably of from one to four carbon atoms.

The compounds of this invention are readily prepared by conventional methods. The asymmetrical peroxide molecule having an alpha-halo acyl group is suitably prepared by a conventional base catalysed reaction between a selected acid chloride and a selected peracid in accordance with the following equation:

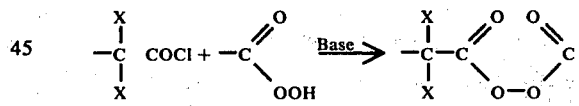

By selecting the appropriate starting materials, various asymmetrical diacyl peroxides may be prepared. It will be appreciated that as an alternative, the alpha-haloacyl group could be the peracid, and the other acyl group the acyl halide. The product would be the same as that shown in the formula.

The alpha-halosubstituted acyclic acyl peracid is prepared by usual halogenation reactions employing an acyl halide and chlorine or bromine.

The following examples are offered by way of illustration and not by way of limitation. (All temperatures not indicated are in centigrade).

EXAMPLE I

Acetyl 2-chlorobutyryl peroxide.

To 9.5 g. (0.05 moles) of 40% peracetic acid in 20 cc. $H_2O$ was added 3.2 g. (0.03 moles) of anhydrous sodium carbonate. The mixture was chilled to −3° C. with stirring and 7.1 g. (0.05 moles) of 2-chlorobutyryl chloride in 30 cc. chloroform added over a period of 8 minutes. After a total of 40 minutes at −3° to −6° C., ether and water were added. The organic phase was separated, washed once with cold 1% KOH solution, once with ice water, and once with cold saturated salt water. The concentrated material weighed 8.2 g., including 2.0 g. of dimethyl phthlate. Product A.O. analysis: theory, 8.14 found, 4.81; 59.1% pure; 49.5% yield.

EXAMPLE II

2-Chlorobutyryl m-chlorobenzoyl peroxide

To 6.4 g. (0.06 moles) anhydrous sodium carbonate in 60 cc. $H_2O$ was added 10.2 g. (0.05 moles) of m-chloroperbenzoic acid of 84.35% purity. The stirred mixture was chilled to −2° C. and 8.5 g. (0.06 moles) 2-chlorobutyryl chloride in 30 cc. chloroform was added over 17 minutes. After a total reaction time of 60 minutes, the reaction was worked up as in Example I and gave 15.2 g. product. Product A.O. analysis: theory, 5.77; found, 5.15; 89.30% pure; 97.7% yield.

As indicated earlier, the present materials are useful for initiation monomers having polymerizable ethylenic or vinyl unsaturation. Typical materials in this class are the aryl substituted olefins, such as styrene, alpha-chlorostyrene, and the like; the acrylic and alpha-substituted acrylic acids, esters, nitriles and amides, such as acrylic acid, acrylonitrile, alpha-methacrylonitrile, methyl acrylate, ethyl acrylate, methacrylamide, and the like; and the vinyl halides, esters, ethers, ketones and heterocyclic vinyl compounds, such as vinyl chloride, vinyl acetate, vinyl propionate, vinyl butyrate, vinylidene chloride, vinyl pyrrolidone, and the like. These monomers, as well as mixtures of two or more of them, can be initiated with the compounds of this invention.

Exceptionally good results have been obtained where the monomer to be polymerized is vinyl chloride. To illustrate the utility for polymerizing vinyl chloride, a series of peroxides shown in the table below were prepared by procedures analogous to the preparation of the materials in Example I and II above.

Vinyl chloride was polymerized with each peroxide listed in accordance with the following procedure: Into a 6½ fluid ounce Coke bottle containing 94.0 g. of frozen dispersing solution was added 0.00094 mole of peroxide and 50.0 g. of vinyl chloride monomer. The Coke bottle was capped, the contents almost melted, and then the bottle was placed in a rotating constant temperature bath for 6 hours at 40° C. After the bottle was cooled, and the excess monomer vented, the polyvinyl chloride (PVC) was filtered, washed, and dried. Results are shown in Table I:

| | | Synthesis Results | | Utility as an Initiator for Vinyl Chloride | |
|---|---|---|---|---|---|
| | Peroxide | % Purity | % Yield | Average PVC Yield, g. | PVC Yield % |
| 1. | Lauroyl Peroxide | — | — | 6.05 | 12.1 |
| 2. | Acetyl 2-Chloropropionyl Peroxide | 91 | 30 | 18.30 | 36.6 |
| 3. | Acetyl 2-Chlorobutyryl Peroxide | — | — | 46.80 | 93.6 |
| 4. | Acetyl 2-Chlorodecanoyl Peroxide | 83 | 83 | 46.35 | 92.7 |
| 5. | Acetyl 2-Bromobutyryl Peroxide | 89 | 54 | 43.05 | 86.1 |
| 6. | Acetyl 2-Bromohexadecanoyl Peroxide | 33 | 44 | 45.30 | 90.6 |
| 7. | Acetyl 3-Chloropropionyl Peroxide | 78 | 44 | 2.65 | 5.3 |
| 8. | Acetyl 4-Chlorobutyryl Peroxide | 99 | 26 | 3.85 | 7.7 |
| 9. | m-Chlorobenzoyl 2-Chlorobutyryl Peroxide | — | — | 40.40 | 80.8 |
| 10. | Acetyl Chloroacetyl Peroxide | 100 | 42 | 1.5 | 3.0 |
| 11. | Acetyl Dichloroacetyl Peroxide | 79 | 43 | 0.1 | 0.2 |
| 12. | Acetyl Trichloracetyl Peroxide | 50 | 26 | 4.95 | 9.9 |
| 13. | Acetyl Polychlorodecanoyl Peroxide[1] | 55 | 52 | 1.0 | 2.0 |
| 14. | Lauroyl Dichloracetyl Peroxide | 73 | 20 | 7.8 | 15.6 |
| 15. | Bis 2-Chlorobutyryl Peroxide | 69 | 73 | 27.15 | 54.3 |
| 16. | Acetyl 2-Chloro-3,5,5-trimethylhexanoyl peroxide | — | — | 49.5 | 98.9 |
| 17. | Acetyl 2-Bromo-3,5,5-trimethylhexanoyl peroxide | — | — | 40.15 | 80.3 |
| 18. | m-Chlorobenzoyl 2-chloro-3,5,5-trimethylhexanoyl peroxide | — | — | 22.3 | 44.6 |
| 19. | m-Chlorobenzoyl 2-chloroisovaleroyl peroxide | — | — | 28.25 | 56.5 |

[1]Randomly substituted at different carbon atoms as distinguished from the substantially 100% alpha carbon substitution of compound No. 4 above.

With respect to the results shown in the table, a comparison with lauroyl peroxide has been made since this material is presently a standard material most commonly being used at this time in the PVC industry. With respect to the performance of the remaining compounds, it is noted that materials containing fewer than 4 carbon atoms in the halo substituted side of a molecule, even where the halo substitution is on the alpha carbon atom, results in a substantially lesser yield than where the compositions of this invention are utilized (compare compound No. 2 with Nos. 3, 4, 5, 6, 9, 16, 17, 18 and 19. Attention is also invited to the symmetrical composition No. 15 which contains the requisite 4 carbon atoms together with alpha halo substitution, differing only from composition No. 3 by its symmetrical configuration. Again the performance of composition No. 3 (provided by this invention) is unexpectedly superior. The α-halobranched chain acyl peroxides having a haloaroyl group as the other acyl group (Nos. 18 and 19) are not as effective as the straight chain counterpart (No. 19), but are still much more effective than lauroyl peroxide.

The compounds Nos. 7, 8, 10, 11, 12, 13 and 14 are closely related to the compositions herein claimed, but omit one or more of the specific requirements of the present compounds. Thus composition No. 7 is beta halo substituted and contains fewer than 4 carbon toms in the halo substituted side of the molecule. Composition 8 contains the requisite number of carbon atoms, but is not substituted in the alpha position. Compositions 10, 11, 12 and 14 do not have the four carbon atom minimum required in the halo substituted side of the molecule. Composition No. 13 is not essentially alpha substituted. In all cases these materials which do not meet the requirements of this invention are substantially inferior as polymerization initiators.

In addition to efficiency as initiators, the new materials of this invention exhibit improved thermal stability, a property of practical importance where the initiators are to be stored and shipped. In a comparison between an asymmetrical diacyl peroxide of this invention and a composition meeting all of the requirements except for the presence of halogen atoms on the alpha carbon atoms on both sides of the molecule rendering it symmetrical, a substantial improvement in thermal stability is demonstrated by the new compound when the two compounds are subjected to a rapid heating test. This test consists of heating approximately 0.35 g. of peroxide in an aluminum block at a rate of 4° C. per minute and observing any evidence of decomposition. Results are as follows:

| 1. | Acetyl 2-chlorobutyryl peroxide, 56.0% pure in DMP* | Vigorous decomposition between 58–73° C., with initial decomposition at 38° C. |
|---|---|---|
| 2. | Bis-2-chlorobutyryl peroxide, 46.0% pure in DMP* | Vigorous decomposition between 36–46° C., with initial decomposition at less than 30° C. |

*dimethyl phthalate

Although the foregoing invention has been described in some detail by way of illustration and example for purposes of clarity of understanding, it is understood that certain changes and modifications may be practiced within the spirit of the invention as limited only by the scope of the appended claims.

What is claimed is:

1. An asymmetrical diacyl peroxide of from six to 20 carbon atoms of the formula:

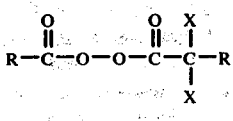

wherein
X is hydrogen, chlorine or bromine, at least one X being chlorine or bromine;
$R^1$ is saturated aliphatic hydrocarbon of from two to 10 carbon atoms, having from zero to five branches along the chain; and
R is a saturated aliphatic or aromatic organic radical of from one to eleven carbon atoms and from zero to three heteroatoms and composed solely of carbon, hydrogen, oxygen as oxy and halogen of atomic number nine to 35, with the proviso that R has at least one atom of oxygen or halogen, when $R^1$ is straight chain.

2. An asymmetrical diacyl peroxide according to claim 1, wherein $R^1$ is branched chain and R has from zero to three halogen atoms.

3. An asymmetrical diacyl peroxide according to claim 1, wherein $R^1$ is straight chain and R has from one to three halogen atoms.

4. An asymmetrical diacyl peroxide according to claim 1, wherein $R^1$ is branched chain and R is aliphatic hydrocarbon of from one to seven carbon atoms.

5. An asymmetrical diacyl peroxide of the formula:

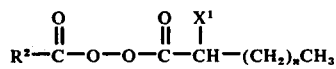

wherein
$X^1$ is chlorine or bromine;
n is an integer of from one to nine;
$R^2$ is a saturated aliphatic or aromatic organic radical having other than alpha-halosubstitution and of from two to seven carbon atoms having from one to three heteroatoms which are halogen of atomic number nine to 35.

6. An asymmetrical diacyl peroxide of the formula:

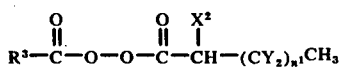

wherein
$X^2$ is chlorine or bromine;
$n^1$ is an integer of from one to six;
Y is hydrogen or alkyl, at least one Y being alkyl, and
$R^3$ is a saturated aliphatic or aromatic organic radical of from one to seven carbon atoms composed solely of carbon, hydrogen, and halogen of atomic number nine to 35, there being not more than three heteroatoms.

7. An asymmetrical diacyl peroxide according to claim 6, wherein from one to three Y's are methyl, the methyl groups being on other than adjacent carbon atoms and $R^3$ is hydrocarbon.

8. An asymmetrical diacyl peroxide according to claim 7, wherein $R^3$ is aliphatic hydrocarbon.

9. An asymmetrical diacyl peroxide according to claim 6, wherein from one to three Y's are methyl and $R^3$ is halohydrocarbon, having from one to three halogens of atomic number nine to 35.

10. m-Chlorobenzoyl 2-chlorobutyryl peroxide.

11. 2-chloro-3,3,5-trimethylhexanoyl acetyl peroxide.

12. 2-bromo-3,3,5-trimethylhexanoyl acetyl peroxide.

* * * * *